United States Patent [19]

Lee et al.

[11] 4,388,056
[45] Jun. 14, 1983

[54] APPARATUS FOR CONTINUOUSLY MAKING AN AIR-LAID FIBROUS WEB HAVING PATTERNED BASIS WEIGHT DISTRIBUTION

[75] Inventors: Franky B. Lee; Orin Jobes, Jr., both of Cincinnati, Ohio

[73] Assignee: The Procter & Gamble Company, Cincinnati, Ohio

[21] Appl. No.: 395,445

[22] Filed: Jul. 6, 1982

Related U.S. Application Data

[63] Continuation of Ser. No. 280,768, Jul. 6, 1981, abandoned, which is a continuation of Ser. No. 176,370, Aug. 8, 1980, abandoned.

[51] Int. Cl.³ .............................................. B29J 1/00
[52] U.S. Cl. ................................................. 425/83.1
[58] Field of Search ....................................... 425/83.1

[56] References Cited

U.S. PATENT DOCUMENTS

| | | | |
|---|---|---|---|
| 3,519,211 | 7/1970 | Sakulich et al. | 241/18 |
| 3,682,761 | 8/1972 | Lee | 161/124 |
| 3,750,962 | 8/1973 | Morgan, Jr. | 241/18 |
| 3,757,785 | 9/1973 | Wosaba | 128/287 |
| 3,766,922 | 10/1973 | Krusko | 128/284 |
| 3,825,194 | 7/1974 | Buell | 241/191 |
| 3,848,598 | 11/1974 | Mesek | 128/287 |
| 3,860,002 | 1/1975 | Kolbach | 128/284 |
| 3,924,626 | 12/1975 | Lee et al. | 128/287 |
| 4,167,404 | 9/1979 | Loeffler et al. | 425/83.1 |
| 4,176,426 | 12/1979 | Neuenschwander | 425/83.1 |

Primary Examiner—James R. Hall
Attorney, Agent, or Firm—Thomas J. Slone; Fredrick H. Braun; Richard C. Witte

[57] ABSTRACT

An apparatus for continuously forming a cyclically contoured and densified air-laid fibrous web having alternately spaced relatively high basis weight narrow regions and relatively low basis weight wide regions. This web can be severed by spaced transverse cuts into uniform, contoured articles such as fibrous absorbent cores for disposable diapers having relatively thick, narrow and absorbent crotch areas; and relatively thin waistband regions. The apparatus comprises means for producing such a web without stepwise basis weight gradients. In one embodiment, the apparatus comprises an air-laying drum having an endless lay down surface which is partially masked to define a plurality of alternately spaced relatively wide areas and relatively narrow areas. The apparatus further comprises air-flow modulating means which can be adjusted to provide a relatively broad range of pressure differentials across the relatively wide areas of the lay down surface while continuously maintaining a relatively fixed, high pressure differential across the relatively narrow areas of the lay down surface. Thus, the relative basis weight (weight of fibers per unit area of the web) of the wide regions of the web can be controlled through a limited range without substantially affecting the basis weight in the relatively narrow regions of the web, and without precipitating any step-wise gradients in basis weight or step-wise changes in thickness; in particular in the machine direction.

10 Claims, 8 Drawing Figures

APPARATUS FOR CONTINUOUSLY MAKING AN AIR-LAID FIBROUS WEB HAVING PATTERNED BASIS WEIGHT DISTRIBUTION

This is a continuation of application Ser. No. 280,768 filed July 6, 1981 now abandoned, which was a continuation of application Ser. No. 176,370 filed Aug. 8, 1980 and now abandoned.

DESCRIPTION

1. Technical Field

This invention relates to apparatus for manufacturing air-laid fibrous webs for such exemplary uses as absorbent cores of disposable diapers.

2. Background Art

U.S. Pat. No. 3,682,761 which issued Aug. 8, 1972 to C. A. Lee et al discloses an apparatus for continuously forming an air-laid web which apparatus includes an array of air flow control valves and discrete chambers disposed subjacent an endless foraminous carrier member; reference FIG. 9. Briefly, the valves and chambers are stationary and provide means for controlling relative flows of air through the various portions or sections of the carrier as they cyclically pass the array of valves and discrete chambers. Thus, when a column of air entrained fibers is directed towards the carrier, and air is drawn through the carrier, discrete chambers, and valves, an air-laid web is formed on the carrier; and the valves and chambers enable making the web have uniform basis weight distribution: uniform weights of fibers for each unit area of the web. Alternatively, it is believed this apparatus would also enable forming an air-laid web having a transverse basis weight gradient albeit no cyclical machine direction basis weight gradients.

U.S. Pat. No. 3,860,002 which issued Jan. 14, 1975 to Charles G. Kolbach discloses a drum type apparatus for continuously forming an air-laid web having discrete thickened areas which are uniformly spaced in the machine direction. In this apparatus, an air-laying drum is provided with two internal vacuum manifolds. A first vacuum manifold underlying the portions of the drum upon which the thin field portions of the air-laid web is formed; and a second vacuum manifold underlying the discrete portions of the drum upon which the discrete thickened areas of the air-laid web is formed. The apparatus further comprises means for independently adjusting or controlling the levels of vacuum in the two manifolds. It is believed that this enables, for instance, maintaining a relatively low degree of vacuum in the first manifold and a relatively high degree of vacuum in the second manifold which will precipitate thin and thick web portions, respectively, when the apparatus is operated. Such a web is characterized by step-wise differences in basis weight distribution rather than smooth transitional zones having gradual basis weight gradients.

U.S. Pat. Nos. 3,519,211 which issued July 7, 1970 to R. M. Sakulich et al; 3,750,962 which issued Aug. 7, 1973 to George Morgan, Jr.; and 3,825,194 which issued July 23, 1974 disclose representative disintegration apparatuses which are used to convert drylap (thick fibrous webs) into a stream of air entrained fibers in air-laying apparatuses.

U.S. Pat. Nos. 3,757,785 which issued Sept. 11, 1973 to Charles L. Wosaba, II; 3,766,922 which issued Oct. 23, 1973 to Evelyn H. Krusko; 3,848,598 which issued Nov. 19, 1974 to Frederick K. Mesek; and 3,924,626 which issued Dec. 9, 1975 to Charles A. Lee et al are representative patents showing disposable diapers having stepped or contoured absorbent cores. These patents discuss the desirability of providing greatest absorbency in the zones which are wetted; and less absorbency in the zones which normally remain relatively dry: e.g., the waistband areas.

As compared to the foregoing background art, the present invention provides an improved apparatus for forming a cyclically side-edge-contoured air-laid web which can, for instance, be subdivided by transverse cuts into discrete, hourglass contoured absorbent cores for disposable diapers, and which absorbent cores have predetermined basis weight gradients from end-to-end (i.e., machine direction as air-laid). That is, absorbent cores having relatively thick, high basis weight crotch areas; and relatively thin, lower basis weight waistband areas; and no step-wise changes in their thickness.

DISCLOSURE OF THE INVENTION

In accordance with one aspect of the present invention, there is provided an improved air-laying apparatus for continuously forming an air-laid fibrous web having oppositely phased, cyclically undulating side edges and a predetermined patterned basis weight distribution which web can be subdivided by transverse cuts into discrete contoured absorbent articles such as absorbent cores of disposable diapers having relatively thick (high average basis weight per unit area) crotch areas, thinner (lower average basis weight per unit area) waistband areas; and no step-wise changes in thickness. The improved apparatus is of the type which includes a lay-down drum having a circumferentially segmented annular-shape plenum comprising a multiplicity of circumferentially spaced transverse plenum segments, a partially masked foraminous laydown surface having oppositely contoured, cyclically undulating side edges defining cyclically circumferentially spaced relatively widely masked and relatively narrowly masked transverse areas of said surface and which areas corporately define the radially outwardly facing boundary of said plenum, and constant differential pressure means for drawing air through said surface and said plenum from an air-entrained-fiber deposition chute as said drum is being rotated on its axis of revolution. The improvement comprises stationary adjustable air flow modulating means disposed adjacent the radially inwardly disposed boundary of an arcuate portion of said plenum circumferentially spanning a plurality of said transverse plenum segments whereby the pressure drop across said relatively widely masked transverse sections of said lay-down surface can be adjusted without substantially affecting the pressure drop across said relatively narrowly masked transverse sections of said lay-down surface.

BRIEF DESCRIPTION OF THE DRAWINGS

While the specification concludes with claims particularly pointing out and distinctly claiming the subject matter regarded as forming the present invention, it is believed the invention will be better understood from the following description taken in conjunction with the accompanying drawings in which:

DETAILED DESCRIPTION OF THE INVENTION

Figure 1:
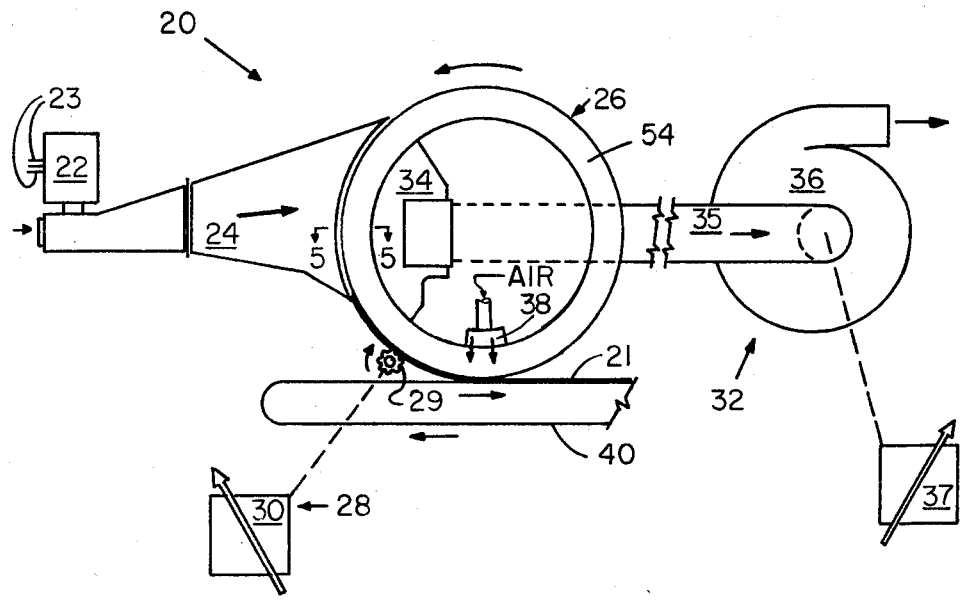
FIG. 1 is a fragmentary, somewhat schematic, side elevational view of an air-laying apparatus embodying the present invention.

An exemplary air-laying apparatus 20 for forming an air-laid web 21, which apparatus embodies the present invention is shown in FIG. 1 to comprise a drylap disintegrator 22 for disintegrating drylap webs 23; an air-entrained-fiber deposition chute 24; an air-laying or laydown drum 26; drive means 28 for the air-laying drum 26 comprising a drive gear 29 and a variable speed drive 30; constant differential pressure means 32 including a vacuum plenum 34, duct 35, fan 36, and a variable-speed fan drive 37; an air-blowoff plenum 38; and a take-away conveyor 40 which is driven in timed relation with drum 26 by means not shown in FIG. 1.

Figure 2:
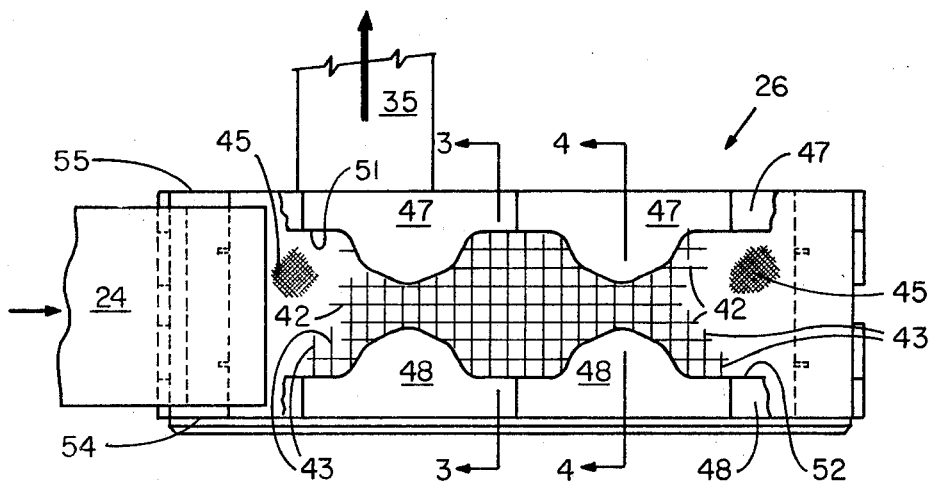
FIG. 2 is an enlarged scale, fragmentary plan view of the central portion of the apparatus shown in FIG. 1.

As shown in FIG. 2, the air-laying drum 26 has a honeycomb type annular-shape frame comprising circumferentially extending ribs 42 and transverse plates 43 which frame is covered on its radially outwardly facing surface by a screen 45. The drum 26 further comprises a front annular wall 54, a back annular wall 55, and a plurality of masking members 47 and 48 which corporately define circumferentially extending, oppositely phased, cyclically undulating edges 51 and 52, respectively. Thus, these elements corporately define an annular shape plenum which plenum is designated 56 in FIG. 3, and which is subdivided into a multiplicity of transverse plenum segments by one-hundred-twenty plates 43 which, in the embodiment shown, are spaced circumferentially 3 degrees between centers. Thus, air flowing towards drum 26 through chute 24 will pass radially inwardly into drum 26 through the screen 45; thence through the plenum segments intermediate chute 24 and duct 35; and thence out of the drum through duct 35. In doing so, fibers entrained in the air are deposited on the portions of screen 45 disposed intermediate edges 51 and 52, and adjacent chute 24. In this manner, referring again to FIG. 1, an air-laid web 21 of fibers is continuously formed as the screened and masked surface of drum 26 passes deposition chute 24; and the web 21 is removed onto take-away conveyor 40 by air flowing radially outwardly through air-blow-off plenum 38.

Figure 3:
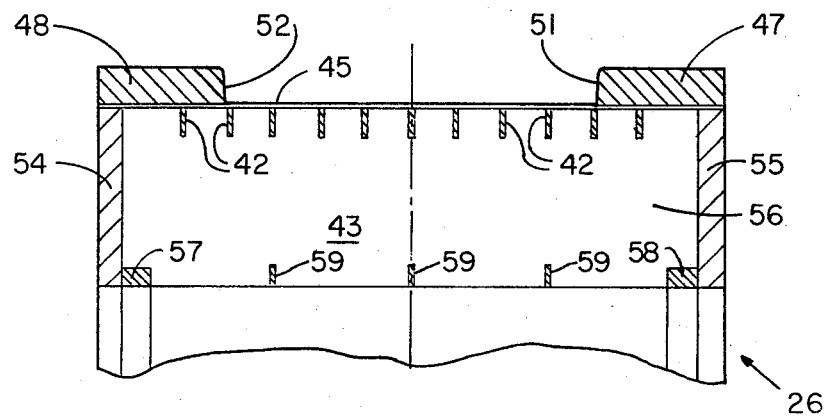
FIGS. 3 and 4 are enlarged scale, fragmentary sectional views taken along lines 3—3, and 4—4, respectively, of FIG. 2.
Figure 4:
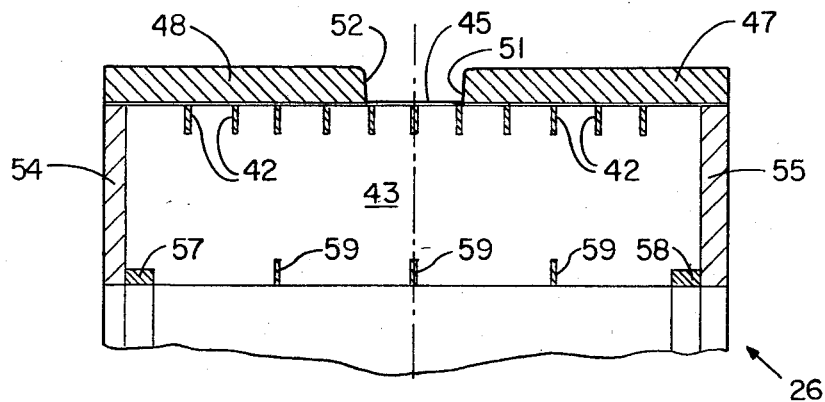

As shown in FIGS. 3 and 4, drum 26 further comprises a front annular wall 54, a back annular wall 55, reinforcing hoops 57 and 58, and three circumferential ribs 59 which ribs are substantially identical to ribs 42 which number eleven in the embodiment of the present invention shown in the figures.

Figure 5:
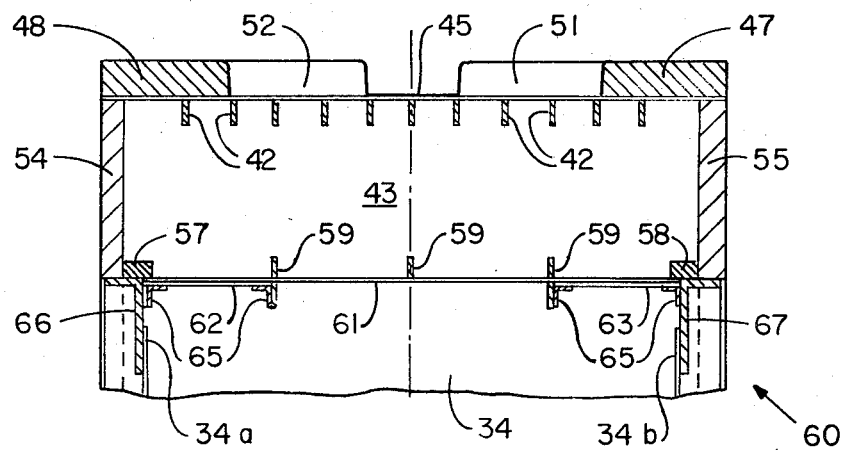
FIG. 5 is an enlarged scale, fragmentary sectional view taken along line 5—5 of FIG. 1.

As shown in FIG. 5, the stationary, adjustable air flow modulating means 60 comprises a fixed position perforated plate 61, two circumferentially adjustable shutter plates 62 and 63, a frame 65, and air-seal rings 66 and 67 and, as shown in FIG. 5, is disposed intermediate the radially inwardly facing boundary of the annular plenum 56 of drum 26 and the walls 34a and 34b of vacuum plenum 34.

Figure 6:
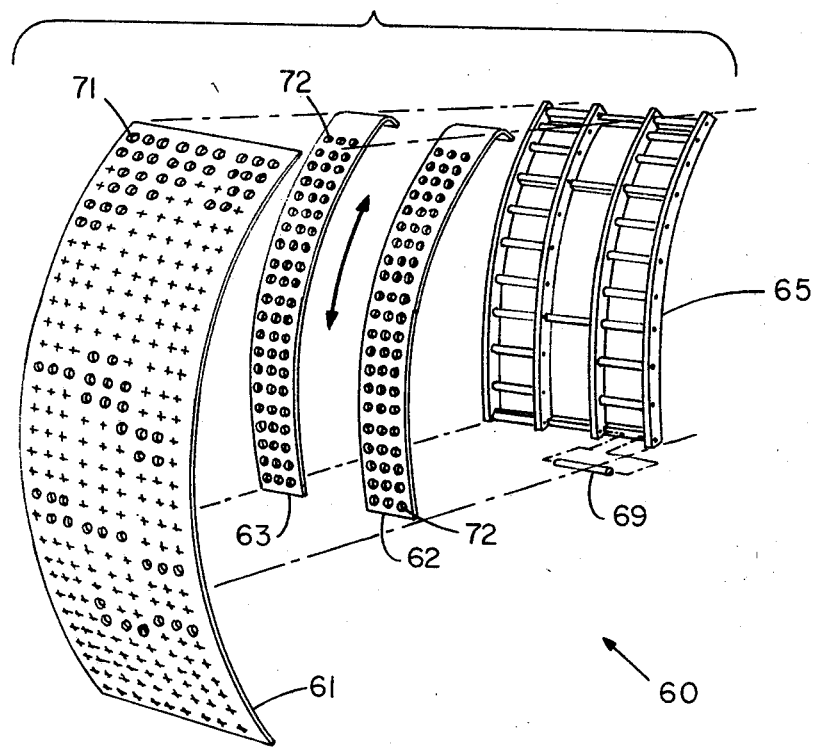
FIG. 6 is an exploded perspective view showing the principal components of an adjustable, arcuate-shape, air-flow shutter mechanism which is incorporated in the apparatus shown in FIG. 1.

The elements of the air flow modulating means 60, FIG. 5, are shown in exploded perspective relation in FIG. 6 in order to more clearly depict the arcuate shapes of perforated plate 61 and the adjustable shutter plates 62 and 63.

As shown in FIG. 6, the perforated plate 61 is curved to conform to an imaginary cylindrical surface which is defined by the radially inwardly disposed transverse edges of transverse plates 43 of drum 26 as it is rotated on its axis. Further, as shown, plate 61 is perforated with an array of apertures 71 which, as shown, are disposed in an orthogonal array comprising 30 horizontal rows and 9 circumferentially extending columns for a total of 270 apertures 71. Nominally, these are preferably one to one-and-one-half inches in diameter and are disposed with center-to-center spacings of two or more times their diameters. Also, in an exemplary embodiment, plate 61 was configured to have a transverse width nominally equal to the transverse dimension of annular plenum 56, and had a length which when installed circumferentially spanned 72 degrees of the annular plenum 56. Thus, in that embodiment, it spanned about 24 of the transverse plenum sectors into which plenum 56 is subdivided by transverse plates 43.

As also shown in FIG. 6, shutter plates 62 and 63 are arcuate shape to conform to the radially inwardly disposed surface of plate 61, and each are about one third the width of plate 61, and somewhat shorter. Both shutters 62 and 63 are perforated by arrays of holes 72 which are sized and spaced identically to the array of apertures 71 in plate 61. However, being shorter and only one-third as wide, shutters 62 and 63 as shown comprise means for modulating the open area through only the circumferentially extending edge portions of assembly 60, FIG. 5. That is, as shown in FIG. 5, the apparatus does not include means for modulating the effective open area of the central portion of plate 61 disposed intermediate shutters 62 and 63, nor any of the lower portion of plate 61.

Referring again to FIG. 6, air flow modulating means 60 is assembled by securing rollers 69 to frame 65 by means not shown so that the rollers are freely rotatable; securing plate 61 to the radially outwardly facing edges of frame 65 by securement means not shown; and by then inserting shutters 62 and 63 between plate 61 and rollers 69 with arcuate motions.

The air flow modulating means 60, FIG. 6, is then secured to vacuum plenum 34, FIG. 1, in the relation shown in FIG. 5 so that all of the air passing radially inwardly through the drum passes through the array of apertures in plate 61; thence into the vacuum plenum 34; and forwarded through duct 35 and exhausted through fan 36. In so doing, part of the air necessarily passes through the holes of shutter plates juxtaposed plate 61.

The disposition of shutters 62 and 63 with respect to plate 61 can be circumferentially adjusted, and secured in position by means not shown, to provide a desired degree of registration between the arrays of holes in shutters 62 and 63, and the adjacent portions of the array of apertures in plate 61. Thus, the effective open areas of the edge portions of plate 61 can be adjusted by circumferentially adjusting or moving shutters 62 and 63.

In the operation of apparatus 20, drylap is reduced to free fibers by disintegrator 23 and entrained in air being drawn through the apparatus by fan 36. The fiber entrained air passes through fiber deposition chute 24 and impinges radially inwardly on the unmasked portions of screen 45. The screen 45 blocks the passage of the fibers causing them to accumulate and continuously form an air-laid web as drum 26 is rotated. The fiber depleted air then passes through the underlying transverse plenum sectors, the air flow modulating means 60, vacuum plenum 34, duct 35, and exhausts from fan 36. The web 21 is dislodged from the screen surface by air flowing through plenum 38 after the web emerges from between chute 24 and vacuum plenum 34. The dislodged web is received by conveyor 40 and forwarded downstream to be rolled or segmented or the like; preferably segmented into discrete hourglass-shape fibrous batts 121, FIGS. 7 and 8, having smooth (non-stepwise) basis weight gradients in the machine direction. These have thick, narrow absorbent crotch portions and relatively thin, wide waistband regions and no stepwise thickness discontinuities as further described hereinafter.

While it is not intended to be bound by a theory of operation, it is believed that the average basis weight of the narrow portions of web 21 (i.e., crotch regions of batts 121) is determined essentially by the combination of rate of feed of drylap 23, and the rate of air flow or pressure differential across the plenum induced by fan 36; and the relative degree of lower basis weight of the wide portions (i.e., waistband regions of batts 121) of web 21 is essentially a function of how open or closed the air flow modulating means are. That is, to what degree the holes of shutters 62 and 63 are in registration or coincidence with the apertures of plate 61: being in registration precipitating the least reduction of basis weight in the wide areas relative to the narrow areas; and being out of registration precipitating the greatest reduction of basis weight in the wide areas relative to the narrow areas. It is believed these relationships are true because: the fan induced pressure drop across the plenum 56 is essentially wholly across the portions of screen 45 spanning transverse plenum sectors subjacent the relatively narrow areas because the composite area of the adjacent apertures in plate 61 are relatively great compared to the open area of the narrow portions of screen 45; and only a portion of the fan induced pressure drop occurs across wider portions of the screen spanning transverse plenum sectors disposed thereunder because part of the pressure drop occurs across the apertures of plate 61 subjacent thereto. Were it not for the air flow modulating means, substantially all portions of the screen 45 would be subjected to a uniform pressure differential which would essentially produce a web having substantially uniform basis weight distribution throughout.

While the exemplary embodiment of the present invention shown in the figures and described hereinabove comprised means for modulating air flow through only the circumferentially extending edge portions of plate 61 and, therefore, plenum 56, it is not intended to thereby limit the present invention. Indeed, one shutter plate equal in size to plate 61 could be used if further flow modulation were required. Also, while it is believed the symmetrical disposition of shutter plates 62 and 63 precipitate the lowest basis weight areas of batts 121 in their end corners (adjacent contour lines 167 in FIG. 7), it is not intended to thereby limit the present invention to such symmetrically disposed air flow modulating means.

Figure 7:
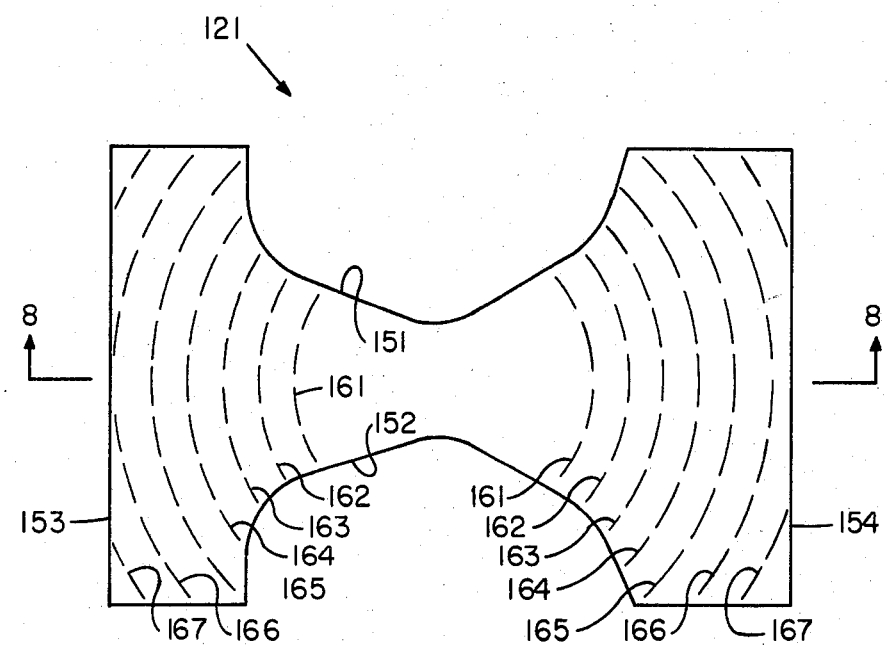
FIG. 7 is a plan view of a discrete fibrous batt of the type which can be produced through the use of apparatus embodying the present invention: for instance, the apparatus shown in FIG. 1.
Figure 8:
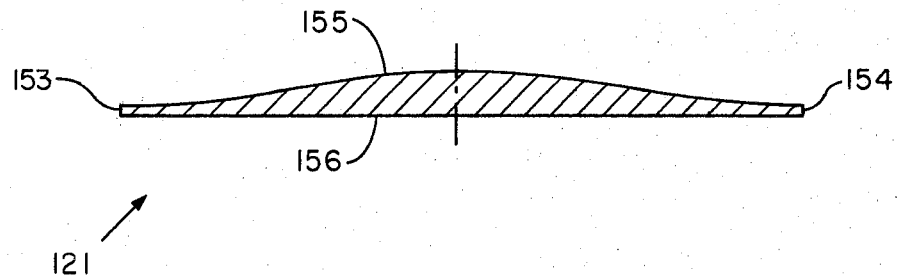
FIG. 8 is a longitudinal sectional view of the fibrous batt shown in FIG. 7 which view is along line 8—8 of FIG. 7.

The air-laid web 21, FIG. 1, is sub-divided into discrete, air-laid fibrous batts 121 of the contoured configuration shown in FIGS. 7 and 8. Batt 121 has side edges 151 and 152, end edges 153 and 154, top surface 155 and bottom surface 156. The arcuate dashed lines 161 through 167, FIG. 7, represent lines of nominally equal basis weights which, as indicated in FIG. 8, are greater in the center portion of the batt 121 than in the portions spaced outwardly therefrom.

An exemplary embodiment of the present invention was constructed in accordance with the foregoing description of apparatus 20 wherein: the diameter of the drum 26 at the laydown surface of screen 45 is about 211 centimeters (about 83 inches) giving the drum a circumference of about 662 centimeters (about 261 inches) on screen 45; masking members 47 and 48 have circumferential lengths of about 66.2 centimeters (about 26 inches) (or an arc length of about 36 degrees of the drum) and are contoured to provide relatively wide unmasked areas (e.g., as along section line 3—3, FIG. 2) which are about 43 centimeters (about 17 inches) wide, and narrow unmasked areas (e.g., as along section line 4—4, FIG. 2) which are about 11.4 centimeters (about 4½ inches) wide. As stated hereinbefore, transverse plates 43 number 120; are spaced circumferentially at 3 degree intervals; and have transverse and radial dimensions of about 61 by 15 centimeters (about 24 by 6 inches), respectively. The air flow modulating means 60 spans the entire width of the drum and 72 degrees of its circumferential length in line with the discharge end of the deposition chute 24. The discharge end of the deposition chute is spaced slightly from the drum to admit a relatively small amount of secondary air flow transverse the masking members 47 and 48 to preclude clumping of fibers thereon. The air flow modulating means 60 circumferentially spans 2 entire discrete batt deposition zones on the drum having 24 transverse plenum segments (a segment being the space between adjacent transverse plates 43). Thus, it is believed that because the air flow modulating means circumferentially spans such a relatively large number of transverse plenum sectors, the fan 36 establishes a relatively constant pressure differential between the deposition chute 24 and vacuum plenum 34: (i.e., across the screen, the intervening transverse plenum sectors, and the air flow modulating means 60). In the narrow areas of the screen 45, most of the differential occurs across screen 45 and the fiber buildup thereon whereas, subjacent the wide areas of screen 45, it is believed a substantial pressure drop occurs across the air flow modulating means 60. Thus, as the drum rotates and each area of screen 45 is exposed to the fiber deposition chute 24 for the same amount of time during each revolution of the drum, the areas of the screen having the largest pressure differential across them (i.e., the narrow areas) experience greater fiber buildups or accumulations than the areas of the screen having lower pressure differentials across them (i.e., the wide areas). Also, because each of the transverse plenum segments span only about one twelfth the circumferential length of each batt, and because the undulating edges 51 and 52 have no stepwise changes, the web 21 formed on apparatus 50 and the absorbent batts 121 formed therefrom have smooth basis weight gradations in the machine direction. That is, no stepwise basis weight or thickness differences. Exemplary absorbent batts 121 have been made using this apparatus which are: about 66.2 centimeters (about 26 inches) in length; have waistband and crotch regions which are about 43 and 11.4 centimeters (about 17 and 4½ inches) wide, respectively; have total fiber weights of about 84 grams and have basis weight distributions of from about 0.04 grams per square centimeter (about 0.25 grams per square inch) in the crotch regions to about 0.03 grams per square centimeter (about 0.17 grams per square inch) in the distal waistband regions. Such batts, when used as absorbent cores for adult incontinent briefs are very absorbent in the crotch areas where most needed, and have reduced absorbency in the waistband regions which normally remain relatively dry.

While the exemplary apparatus has been described with respect to one size and one weight of absorbent batts, it can, of course, be modified by changing the masking members, the rate of drylap feed, the rate of air flow, and the air flow modulating means to produce similar articles of different sizes, weights, and basis weight distributions.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. In an improved apparatus for continuously forming an air-laid fibrous web having oppositely phased, cyclically undulating side edges and a predetermined patterned basis weight distribution which apparatus includes a laydown drum having a forming surface, means for forming and directing a column of air entrained fibers onto said forming surface and depositing fibers on said forming surface, and air flow inducing means for drawing fiber-depleted air through said surface and exhausting it, said laydown drum having a circumferentially segmented annular-shape plenum comprising a multiplicity of circumferentially spaced transverse plenum segments, a partially masked foraminous laydown surface having oppositely contoured, cyclically undulating side edges defining cyclically circumferentially alternately spaced relatively widely masked and relatively narrowly masked sections of said surface and which sections corporately define the radially outwardly facing boundary of said plenum, and said air flow inducing means including constant differential pressure means for drawing air through said surface and said plenum from an air-entrained-fiber deposition chute as said drum is being rotated on its axis of revolution, the improvement comprising stationary adjustable air flow modulating means disposed adjacent the radially inwardly disposed boundary of an arcuate portion of said plenum circumferentially spanning a plurality of said transverse plenum segments so that the pressure drop induced by said means for drawing air through said surface can be adjusted across said relatively widely masked transverse sections of said lay-down surface without substantially affecting the pressure drop induced across said relatively narrowly masked transverse sections of said lay-down surface.

2. The improved apparatus of claim 1 wherein said stationary adjustable air flow modulating means comprises a stationary perforated plate having an array of apertures therethrough, a juxtaposed adjustable-position shutter plate having a field of holes therethrough disposed in corresponding relation to a portion of said array, and means for adjusting the position of said shutter plate with respect to said stationary plate to vary the degree of registration of the field of holes with the apertures of said portion of said array whereby the total effective open area of said stationary plate can be varied through a predetermined range.

3. The improved apparatus of claim 2 wherein said field of holes is substantially identical to the entire said array of apertures whereby the total open area of said stationary plate can be varied from full closed to the full composite open area of said array of apertures.

4. The improved apparatus of claim 2 further comprising a second shutter plate substantially identical to said shutter plate, and means for adjustably positioning them in transverse spaced relation and justaposed the oppositely disposed machine-direction edge portions of said stationary plate, said shutter plates being configured to be less than half the width of said stationary plate so that the shutter plates only provide means for modulating the air-flow through the machine-direction extending edge portions of the stationary plate and leave a machine-direction extending central portion of said array of apertures in said stationary plate unmodulated.

5. The improved apparatus of claim 1, 2, or claim 4 further comprising means for varying the fiber density in the column of fiber entrained air, and means for varying the rate of air flow through said laydown surface to control the average basis weight of said web formed on said relatively narrow areas of said laydown surface substantially independently from adjusting said shutter plate whereby adjusting said shutter plate will effectively control the degree of lesser basis weight of the portions of said web formed on the relatively wider areas of said laydown surface.

6. In an improved apparatus for continuously forming an air-laid fibrous web having oppositely phased, cyclically undulating side edges which apparatus includes a laydown drum having a forming surface, means for forming and directing a column of air entrained fibers onto said forming surface and depositing fibers on said forming surface, and air flow inducing means for drawing fiber-depleted air through said surface and exhausting it, said laydown drum having a circumferentially segmented annular-shaped plenum comprising a multiplicity of circumferentially spaced transverse plenum segments, a partially masked foraminous laydown surface having oppositely contoured, cyclically undulating side edges defining cyclically circumferentially alternately spaced relatively widely masked and relatively narrowly masked sections of said surface and which sections corporately define the radially outwardly facing boundary of said plenum, and said air flow inducing means including constant differential pressure means for drawing air through said surface and said plenum from an air-entrained-fiber deposition chute as said drum is being rotated on its axis of revolution, the improvement comprising air flow modulating means disposed inwardly of said transverse plenum segments so that the pressure drop through said surface can be adjusted across said lay-down surface such that the air-laid fibrous web has a predetermined patterned basis weight distribution.

7. The improved apparatus of claim 6 wherein said air flow modulating means comprises a stationary perforated plate having an array of apertures therethrough, a juxtaposed adjustable-position shutter plate having a field of holes therethrough disposed in corresponding relation to a portion of said array, and means for adjusting the position of said shutter plate with respect to said stationary plate to vary the degree of registration of the field of holes with the apertures of said portion of said array whereby the total effective open area of said stationary plate can be varied through a predetermined range.

8. The improved apparatus of claim 7 wherein said field of holes is substantially identical to the entire said array of apertures whereby the total open area of said stationary plate can be varied from full closed to the full composite open area of said array of apertures.

9. The improved apparatus of claim 7 further comprising a second shutter plate substantially identical to said shutter plate, and means for adjustably positioning them in transverse spaced relation and juxtaposed the oppositely disposed machine-direction edge portions of said stationary plate, said shutter plates being configured to be less than half the width of said stationary plate so that the shutter plates only provide means for modulating the air-flow through the machine-direction extending edge portions of the stationary plate and leave a machine-direction extending central portion of said array of apertures in said stationary plate unmodulated.

10. The improved apparatus of claim 6, 7, or claim 9 further comprising means for varying the fiber density in the column of fiber entrained air, and means for varying the rate of air flow through said laydown surface to control the average basis weight of said web formed on said relatively narrow areas of said laydown surface substantially independently from adjusting said shutter plate whereby adjusting said shutter plate will effectively control the degree of lesser basis weight of the portions of said web formed on the relatively wider areas of said laydown surface.

* * * * *